United States Patent [19]

Nadzan et al.

[11] 4,432,985
[45] Feb. 21, 1984

[54] N-ALKYLATED CARBOXYLIC ACID DERIVATIVES AS ANTI-CONVULSANT AGENTS

[75] Inventors: Alex M. Nadzan, Gurnee; George R. Granneman, Lindenhurst, both of Ill.

[73] Assignee: Abbott Laboratories, North Chicago, Ill.

[21] Appl. No.: 358,167

[22] Filed: Mar. 15, 1982

[51] Int. Cl.³ .................. A61K 31/445; C07D 211/14
[52] U.S. Cl. .................... 424/267; 424/274; 424/311; 424/320; 424/322; 546/245; 546/247; 546/248; 548/531; 548/538; 548/568; 548/573
[58] Field of Search ............... 546/245, 247, 248; 548/531, 538, 568, 573; 424/267, 274, 311, 320, 322

[56] References Cited

PUBLICATIONS

Chemical Abstracts, 65:15345c (1966) [Neth. Appl. 6,514,223, Sandoz, 5/6/66].
Chemical Abstracts, 57:16573b (1962) [Belg. 611,643, Bayer, 6/18/62].
Chemical Abstracts, 54:11012d (1960) [Nazarov et al., Zhur. Obshchei Khim., 29,2508-12 (1959)].
Chemical Abstracts, 77:151943a (1972) [Fr. Demande 2,095,399, Tilles, 3/17/72].
Chemical Abstracts, 89:101904r (1978) [Japan Kokai 7824,023, Fujimoto et al., 3/6/78].
Conant; J., The Chemistry of Organic Compounds, MacMillan, New York, 1939, p. 264.

Primary Examiner—Richard A. Schwartz
Attorney, Agent, or Firm—Dennis K. Shelton; Martin L. Katz

[57] ABSTRACT

Described are compounds of the formula

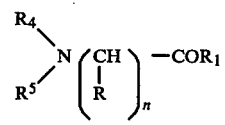

wherein R is hydrogen or loweralkyl; $R_1$ is $-OR_2$ or $-NR_2R_3$ wherein $R_2$ and $R_3$ independently of one another denote hydrogen or loweralkyl; n is 0 or 1; $R_4$ and $R_5$ independently of one another denote loweralkyl or together form a 5 or 6 membered cycloalkyl substituted by hydrogen or loweralkyl, and together with the nitrogen atom, form a ring; and pharmaceutically acceptable salts thereof and their use as anticonvulsant agents in a method of controlling convulsions or seizures.

15 Claims, No Drawings

N-ALKYLATED CARBOXYLIC ACID DERIVATIVES AS ANTI-CONVULSANT AGENTS

BACKGROUND OF THE INVENTION

Dipropylacetic acid (valproic acid) is a common broad spectrum anti-convulsant drug effective in the prevention of seizures. In rare cases, there have been incidents of hepatotoxicity experienced by patients being treated with the drug. As a result, there is an increasing level of interest in the relationship of hepatic toxicity with valproic acid and its metabolites.

The primary routes in the extensive metabolism of valproic acid (VPA) are mitochrondrial $\beta$-oxidation and microsomal glucuronidation. The hepatotoxicity of VPA is mediated through the unsaturated metabolites: (A) 2-propylpent-4-enoic acid (4-en-VPA), 2-propylpent-3-enoic acid (3-en-VPA) and 2-propylpenta-2,4-dienoic acid (2,4-dien-VPA), which are formed after omega and omega-1 oxidation of VPA in the endoplasmic reticulum, and (B) 2-propylpent-2-enoic acid (2-en-VPA), which is formed by $\beta$-oxidation in the mitochondria. As is the case with the well-characterized hepatotoxins, hypoglycin A and pent-4-enoic acid, excessive amounts of these metabolites are thought to primarily affect mitochondrial function by inhibition of one or more enzymes in the $\beta$-oxidation sequence, and/or depletion or sequestration of either carnitine or coenzyme A, or both. The inhibition of $\beta$-oxidation leads to diversion of fatty acids, first producing dicarboxylicaciduria, then microvesicular steatosis, while also affecting mitochondrial energetics and processes dependent thereupon. Mitrochondrial inhibition and depletion of glycogen stores can ultimately lead to enhanced production of the en-VPA metabolites, creating a vicious cycle leading to fulminant hepatitis and death. In the majority of patients receiving valproic acid, the extent of formation of these metabolites is minimal; however, in some patients, particularly those receiving concomitant medication capable of inducing enzymes in the endoplasmic reticulum, the amount of the metabolites is greater, causing transient but reversible changes in hepatic function indicators. In rare cases, due to excessive levels of the metabolites or due to individual susceptibility caused by genetic mitochondrial defects, defects in glucuronidation, trauma, hepatotoxins or other exacerbating circumstances, compensation for the presence of the metabolites does not occur, and severe hepatotoxicity ensues.

In any event, the availability of compounds which do not exhibit hepatotoxicity is desirable.

SUMMARY OF THE INVENTION

The present invention provides compositions and a method for the treatment of seizures and is directed to compounds of the formula

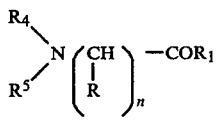

wherein R is hydrogen or loweralkyl; $R_1$ is $-OR_2$ or $-NR_2R_3$ wherein $R_2$ and $R_3$ independently of one another denote hydrogen or loweralkyl; n is 0 or 1; $R_4$ and $R_5$ independently of one another denote loweralkyl or together form a 5 or 6 membered cycloalkyl substituted by hydrogen or loweralkyl, and together with the nitrogen atom, form a ring, and pharmaceutically acceptable salts thereof.

Included are compounds of the formula

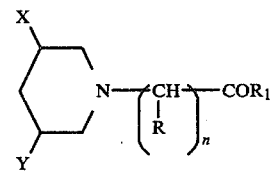

and of the formula

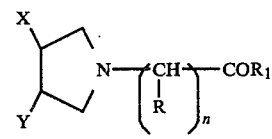

wherein X and Y are loweralkyl.

These compounds are designed to supress $\beta$, omega and omega-1 oxidation metabolites.

The term "loweralkyl" as used herein refer to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "pharmaceutically acceptable salts" includes nontoxic salts of the compounds of the invention which are generally prepared by reacting the free acid with a suitable organic or inorganic base. Representative salts include ammonium, alkyl ammonium, or amine derived salts and metallic salts such as the sodium, potassium, calcium or magnesium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage forms. For oral administration, amounts of from about 0.1 to 200 mg/kg per day per patient are useful, with the total dose of up to 0.5 to 5.0 gm per day being a suitable range for large animals, including humans.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

The disubstituted amine derivatives of this invention can be prepared by reductive alkylation of an appropriate aminoacid derivative with an aldehyde in the presence of hydrogen on palladium.

Alternatively, some of the above compounds may be prepared by reaction of the appropriate amine with an α-haloacid or ester in the presence of excess amine. In the case of ester, saponification with aqueous base, followed by neutralization with acid provides the desired substituted acid.

Substituted urea derivatives can be made by reaction of an appropriate amine with trimethylsilyl isocyanate followed by aqueous hydrolysis of the resulting trimethylsilylurea.

In order to illustrate the manner in which the above compounds can be prepared and the properties of the compounds, reference is made to the following examples, which, however, are not meant to limit or restrict the scope of the invention in any request.

EXAMPLE 1

N,N-Dipropyl Glycine

Glycine (1 mol) is stirred in an atmosphere of hydrogen at room temperature in aqueous ethanol in the presence of propanal (4 mol) and palladium on charcoal (10% Pd-C) until the absorption of hydrogen ceases. The reaction mixture is filtered and the solution is evaporated to dryness, in vacuo. The resulting solid amino acid is crystallized from acetone-petroleum ether to provide N,N-dipropyl glycine.

EXAMPLE 2

2-(N,N-Dipropylamino)Hexanoic Acid

2-Aminohexanoic acid (1 mol) is treated with excess propanal (4 mol) under the conditions described in Example 1 to give 2-(N,N-dipropylamino hexanoic acid as an off-white solid.

EXAMPLE 3

N,N-Dipropyl Urea

A solution of trimethyl isocyanate (1 mol) in ether is added over 30 minutes to a stirred solution of dipropylamine (1.6 mol) in ether. The reaction mixture is heated at reflux for 1 hour, then concentrated and cooled to −20° C. to induce crystallization. The resulting solid is hydrolyzed by stirring with a mixture of ether and water at 40° for 4 hours. Separation of the two layers, followed by concentration of the aqueous phase affords N,N-dipropyl urea as a white solid.

EXAMPLE 4

2-[3,5-Dimethylpiperidinyl)]acetic acid 3,5-Dimethylpiperidine (0.22 mol) in ethyl ether is treated at room temperature with methyl 2-chloroacetate (0.1 mol). After several hours of stirring, 3,5-dimethylpiperidine hydrochloride is removed by filtration and the filtrate is concentrated in vacuo to give methyl 2-[1-(3,5-dimethylpiperidinyl)]acetate. The ester is purified by distillation under reduced pressure.

Saponification of the above ester in aqueous sodium hydroxide solution (20%) at reflux, followed by neutralization of the reaction mixture with acid, provides 2-[(3,5-dimethylpiperidinyl)]acetic acid, which is purified by crystallization from chloroform.

EXAMPLE 5

2-[1-(3,4-Dimethylpyrrolidinyl)]acetic acid

The title compound is prepared by treating 3,4-dimethylpyrrolidine (0.22 mol) with methyl 2-chloroacetate (0.1 mol) under the conditions described in Example 4.

EXAMPLE 6

[1-(3,5-Dimethylpiperidinyl)]carboxamide

Reaction of trimethylsilyl isocyanate (1 mol) with 3,5-dimethylpiperidine, using the procedure described in Example 3, provides [1-(3,5-dimethylpiperidinyl)]carboxamide.

EXAMPLE 7

[1-(3,4-Dimethylpyrrolidinyl)]carboxamide

Using the method described in Example 3, the title compound is obtained from 3,4-dimethylpyrrolidine and trimethylsilyl isocyanate.

The anticonvulsant properties of the compounds of this invention can be ascertained by the audiogenic seizure test procedure which is conducted as follows:

Male albino mice are used because of their genetic susceptibility to sound-induced (audiogenic) seizures. Each dose of test compound is administered to 10 mice ½ hour before the animals are tested, 5 at a time, in the audiogenic seizure apparatus. The apparatus is a 2-compartment chamber similar to the one described by Plotnikoff and Green (*Pharmacol. Exp. Therap.*, 119:294, 1957). The inner chamber is constructed of galvanized tin and has 2 doorbells attached to one of its walls. Convulsions are produced by activating the bells electrically for 1 minute. The outer chamber is a double-layered wooden enclosure that serves to attenuate sound level. The mice are observed through a window for the presence of seizure activity and/or fatalities. A seizure is defined as the presence of tonic extensor, tonic flexor and/or clonic convulsions. Protection is measured by blockade of seizures during the 1 minute auditory stimulus. Protective dose 50's (PD 50's) against seizures is determined by probit analysis.

What is claimed is:

1. A compound of the formula

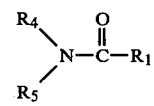

wherein $R_1$ is $-NR_2R_3$ wherein $R_2$ and $R_3$ independently of one another denote hydrogen or loweralkyl, $R_4$ and $R_5$ together with the nitrogen atom form a 5 or 6 membered saturated ring substituted by loweralkyl, or a pharmaceutically acceptable salt thereof.

2. The compound of claim 1: [1-(3,5-dimethylpiperidinyl)]carboxamide.

3. The compound of claim 1: 1-(3,4-dimethylpyrrolidinyl)carboxamide.

4. A pharmaceutical composition useful as an anticonvulsant which comprises an effective amount of a compound of the formula

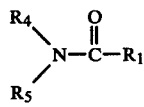

wherein $R_1$ is —$NR_2R_3$ wherein $R_2$ and $R_3$ independently of one another denote hydrogen or loweralkyl; $R_4$ and $R_5$ together with the nitrogen atom form a 5 or 6 membered saturated ring substituted by loweralkyl; or a pharmaceutically acceptable salt thereof, and a pharmaceutically acceptable carrier.

5. The composition of claim 4 wherein the compound is: [1-(3,5-dimethylpiperidinyl)]carboxamide.

6. The composition of claim 4 wherein the compound is: 1-(3,4-dimethylpyrrolidinyl)carboxamide.

7. A method of controlling convulsions or seizures comprising administering to a patient in need of such treatment a therapeutically effective amount of a compound of the formula

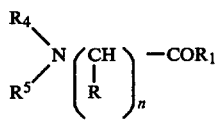

wherein R is hydrogen or loweralkyl; $R_1$ is —$OR_2$ or —$NR_2R_3$ wherein $R_2$ and $R_3$ independently of one another denote hydrogen or loweralkyl; n is 0 or 1; $R_4$ and $R_5$ independently of one another denote loweralkyl or together with the nitrogen atom form a 5 or 6 membered saturated ring which may be substituted by loweralkyl; or a pharmaceutically acceptable salt thereof.

8. The method of claim 7 wherein R is hydrogen or loweralkyl, $R_1$ is $OR_2$ wherein $R_2$ is hydrogen, or —$NR_2R_3$ wherein $R_2$ and $R_3$ are both hydrogen, n is 0 or 1, $R_4$ and $R_5$ are loweralkyl.

9. The method of claim 8 wherein R is hydrogen, $R_1$ is $OR_2$ wherein $R_2$ is hydrogen, n is 1, $R_4$ and $R_5$ are n-propyl.

10. The method of claim 8 wherein R is butyl, $R_1$ is —$OR_2$ wherein $R_2$ is hydrogen, n is 1, $R_4$ and $R_5$ are n-propyl.

11. The method of claim 8 wherein $R_1$ is —$NR_2R_3$ wherein $R_2$ and $R_3$ are both hydrogen, n is 0, $R_4$ and $R_5$ are n-propyl.

12. The method of claim 7 wherein the compound is 2-[1-(3,5-dimethylpiperidinyl)]acetic acid.

13. The method of claim 7 wherein the compound is 2-[1-(3,4-dimethylpyrrolidinyl)]acetic acid.

14. The method of claim 7 wherein the compound is [1-(3,5-dimethylpiperidinyl)]carboxamide.

15. The method of claim 7 wherein the compound is 1-(3,4-dimethylpyrrolidinyl)carboxamide.

* * * * *